United States Patent [19]
Tseng et al.

[11] Patent Number: 5,723,132
[45] Date of Patent: Mar. 3, 1998

[54] SUSTAINED-RELEASE MATRICES FOR DENTAL APPLICATION

[75] Inventors: Mingchih M. Tseng, Hingham; Carl M. Philbrook, Jamaica Plain, both of Mass.

[73] Assignee: Gillette Canada Inc., Kirkland, Canada

[21] Appl. No.: 467,556

[22] Filed: Jun. 6, 1995

Related U.S. Application Data

[62] Division of Ser. No. 262,961, Jun. 21, 1994, which is a division of Ser. No. 898,471, Jun. 15, 1992, Pat. No. 5,340,581, which is a continuation-in-part of Ser. No. 749,137, Aug. 23, 1991, abandoned.

[51] Int. Cl.⁶ .............................. A61K 7/16; A61K 9/22; A61K 9/26; A46B 11/00
[52] U.S. Cl. .................. 424/401; 424/486; 424/487; 15/104.94; 15/160; 15/167.1; 15/109.93; 132/162; 132/163; 132/313; 132/319
[58] Field of Search ........................ 15/104.94, 160, 15/167.1, 109.93; 132/162, 163, 313, 319, 401; 424/486, 487

[56] References Cited

U.S. PATENT DOCUMENTS

| | | |
|---|---|---|
| 21,197 | 9/1858 | Hill et al. . |
| 259,268 | 10/1882 | Gordijn et al. . |
| 639,376 | 12/1899 | Goehring . |
| 846,900 | 5/1907 | Bloom . |
| 1,411,681 | 4/1922 | Burlew . |
| 1,673,638 | 6/1928 | Peterson . |
| 2,099,888 | 11/1937 | Hill et al. . |
| 2,216,333 | 10/1940 | White et al. . |
| 2,304,478 | 12/1942 | Rosenzweig . |
| 2,386,085 | 10/1945 | Babel . |
| 2,667,443 | 1/1954 | Ashton et al. . |
| 2,670,489 | 3/1954 | Cross et al. . |
| 2,880,129 | 3/1959 | Billings et al. . |
| 2,901,392 | 8/1959 | Cohen et al. . |
| 2,938,814 | 5/1960 | Cohen et al. . |
| 2,939,164 | 6/1960 | Rosenthal . |
| 2,965,912 | 12/1960 | Cohen et al. . |
| 3,067,218 | 2/1962 | Cook et al. . |
| 3,162,572 | 12/1964 | Granquist et al. . |

(List continued on next page.)

FOREIGN PATENT DOCUMENTS

| | | |
|---|---|---|
| 0244118 | 4/1987 | European Pat. Off. . |
| 259268 | 10/1926 | United Kingdom . |
| 2024082 | 5/1978 | United Kingdom . |

OTHER PUBLICATIONS

Mathiowitz et al., "Polyanhydride microspheres: 3. Morphology and characterization of systems made by solvent removal", *Polymer*, 31 (Mar. 1990) 547–555.

Torchilin et al., "Targeted accumulation of polyethylene glycol–coated immunoliposomes in infarcted rabbit myocardium", *The FASEB Journal*, 6 (Jun. 1992) 2716–2719.

Müller et al., "Camouflage nanospheres: a new approach to bypassing phagocytic blood clearance by surface modified particulate carriers", *Pharm. Pharmacol Lett*, 3 (1993) 67–70.

Blume et al., "Specific targeting with poly(ethylene glycol)–modified liposomes: coupling of homing . . . ", *Biochimica et Biophysica Acta*, 1149 (1993) 180–184.

Sparks, Memo regarding Gillette Project Descriptions, (Jun. 22, 1994).

Heller et al., "In Vitro and In Vivo Release of Levonorgestrel from Poly(orthoesters)", *Journal of Controlled Release*, 1 (1985) 225–232.

(List continued on next page.)

*Primary Examiner*—Shep K. Rose
*Attorney, Agent, or Firm*—Fish & Richardson P.C.

[57] ABSTRACT

A sustained-release matrix for dental application includes either an anti-microbial agent or a colorant that is released from the matrix when the matrix contacts water. The preferred matrices include a water-soluble polymer and a water-insoluble support resin.

13 Claims, 2 Drawing Sheets

U.S. PATENT DOCUMENTS

| | | | |
|---|---|---|---|
| 3,258,805 | 7/1966 | Rossnan | 15/110 |
| 3,380,848 | 4/1968 | Horowitz et al. . | |
| 3,699,979 | 10/1972 | Muhler et al. . | |
| 3,771,536 | 11/1973 | Dragan . | |
| 3,810,479 | 5/1974 | Miles | 132/84 |
| 3,830,247 | 8/1974 | Kaphalakos . | |
| 3,833,008 | 9/1974 | Blackett, Jr. | 132/85 |
| 3,879,844 | 4/1975 | Griffiths | 30/34 A |
| 3,897,795 | 8/1975 | Engel . | |
| 3,934,001 | 1/1976 | Watson . | |
| 3,943,949 | 3/1976 | Ashton et al. . | |
| 3,960,757 | 6/1976 | Morishita et al. . | |
| 3,978,206 | 8/1976 | Naumann et al. . | |
| 3,991,766 | 11/1976 | Schmitt et al. . | |
| 3,992,336 | 11/1976 | Faucher et al. | 132/7 |
| 4,018,729 | 4/1977 | Faucher et al. | 132/7 |
| 4,033,365 | 7/1977 | Klepak et al. . | |
| 4,170,821 | 10/1979 | Booth . | |
| 4,307,739 | 12/1981 | Chern | 132/85 |
| 4,411,041 | 10/1983 | Braga . | |
| 4,479,501 | 10/1984 | Chern | 132/85 |
| 4,517,703 | 5/1985 | Koke . | |
| 4,586,255 | 5/1986 | Jacobson . | |
| 4,624,051 | 11/1986 | Aprille, Jr. et al. . | |
| 4,685,883 | 8/1987 | Jernberg . | |
| 4,780,320 | 10/1988 | Baker . | |
| 4,802,255 | 2/1989 | Breur et al. | 15/167.1 |
| 4,834,076 | 5/1989 | Millet et al. | 15/104.93 |
| 4,837,007 | 6/1989 | Duckworth et al. . | |
| 4,856,541 | 8/1989 | Kellett et al. . | |
| 4,861,627 | 8/1989 | Mathiowitz et al. . | |
| 4,872,263 | 10/1989 | Etheredge, III . | |
| 4,875,287 | 10/1989 | Creasy et al. . | |
| 4,892,736 | 1/1990 | Goodman . | |
| 4,904,479 | 2/1990 | Illum . | |
| 4,941,487 | 7/1990 | VanBeneden . | |
| 4,978,391 | 12/1990 | Jones . | |
| 4,980,150 | 12/1990 | Keith . | |
| 4,986,288 | 1/1991 | Kent et al. . | |
| 5,002,075 | 3/1991 | Kellett et al. . | |
| 5,015,504 | 5/1991 | Gent et al. . | |
| 5,016,106 | 5/1991 | Kent . | |
| 5,061,106 | 10/1991 | Kent | 15/104.94 |
| 5,098,711 | 3/1992 | Hill et al. . | |
| 5,252,577 | 10/1993 | Brewer et al. | 514/270 |
| 5,300,290 | 4/1994 | Spencer | 15/197.1 |
| 5,313,909 | 5/1994 | Tseng et al. | 45/167.1 |
| 5,320,842 | 6/1994 | Spencer | 424/401 |
| 5,340,581 | 8/1994 | Tseng, et al. | 424/401 |

OTHER PUBLICATIONS

Holland et al., "Polymers for a Biodegradable Medical Devices. 1. The Potential of Polyesters as Controlled Macromolecular Release Systems", *Journal of Controlled Release*, 4 (1986) 155–180.

Mathiowitz et al., "Polyanhydride Microspheres as Drug Carriers. II. Microencapsulation by Solvent Removal", *Journal of Applied Polymer Science*, 35 (1988) 755–774.

SUSTAINED-RELEASE MATRICES FOR DENTAL APPLICATION

This is a divisional of application Ser. No. 08/262,961 filed on Jun. 21, 1994, which in turn is a divisional of Ser. No. 07/898,471 filed on Jun. 15, 1992, now U.S. Pat. No. 5,340,581, which in turn is a continuation-in-part of Ser. No. 07/749,137 filed on Aug. 23, 1991, now abandoned, by Mingchin M. Tseng and Carl M. Philbrook for SUSTAINED-RELEASE MATRICES FOR DENTAL APPLICATION.

BACKGROUND OF THE INVENTION

The invention relates to sustained-release matrices.

Most humans suffer from tooth decay and/or periodontal disease caused by bacteria in the mouth. As a result, decreasing the number of bacteria in the mouth has long been the target of persons working in the health care field. The most common way of minimizing the number of bacteria is to brush and floss the teeth regularly, and to visit a dental hygienist to have the teeth and gums cleaned thoroughly. Another prior approach is oral rinsing, including with a solution containing a known anti-microbial agent like chlorhexidine digluconate.

After a toothbrush has been used, there are a large number of bacteria clinging to the bristles, even after the brush has been rinsed. This, of course, is undesirable, and these bacteria typically will multiply on the bristles between uses. To counter this problem, self-sterilizing toothbrushes have been described in the prior art. One such self-sterilizing toothbrush is described by White et al., U.S. Pat. No. 2,216,333, and includes a combination of a water soluble salt (e.g., sodium carbonate) with an anti-microbial agent (e.g., sulfur). The two are fused to a solid hard body and attached to the head of the toothbrush at the base of the bristles. When exposed to water the sodium carbonate dissolves, forming an alkaline solution that in turn dissolves some sulfur, which kills bacteria.

Toothbrushes wear out with extended use. Breuer et al., U.S. Pat. No. 4,802,255, describe a toothbrush that includes filaments that release a dye, and thus change color, in response to increased use of the filament. The change in color provides a means for monitoring the degree of wear of the toothbrush.

Kent, U.S. Pat. No. 5,061,106, describes including capsules or microspheres in the tuft holes in which the bristles of a toothbrush are mounted. The capsules or microspheres include a disinfectant or medicant that is released during use. A dye may also be included in the structures. The dye also is released over time to enable the user to become aware of when the contents of the capsules are depleted.

SUMMARY OF THE INVENTION

The invention features sustained-release matrices that are particularly suited for use with toothbrushes. The matrices can include an anti-microbial agent that is released over time when the matrices are exposed to water. The matrices may also include a colorant and a water-leachable substance that is released over time when the matrices are exposed to water to cause the matrix to change color.

In one aspect the invention features an oral brush that includes a sustained-release matrix made from a support resin, a water-soluble substance (preferably a water-soluble polymer), and an anti-microbial agent. When the matrix contacts water, the water-soluble substance dissolves, causing the release of the anti-microbial agent.

An oral brush, as used herein, is any brush that includes a handle and a head attached to a brush designed for insertion into the mouth. The brush portion preferably is made from the common bristles found in toothbrushes, but can also be designed for massaging the gums rather than the teeth. For example, Kaminski et al., U.S. Ser. No. 07/724, 129, which was filed on Jul. 1, 1991, is assigned to the same assignee as the present application and is hereby incorporated by reference, describes an interdental foam brush in which the brush portion is made of a soft polyurethane foam.

A support resin, as used herein, is an essentially water-insoluble polymer that provides structural integrity to the matrix as the other components of the matrix—the water-soluble polymer and anti-microbial agent—dissolve or leach out. A further description of what constitutes a support resin is included in the Other Embodiments section. Preferably, the polymer used as the support resin should have a low processing temperature (less than 130° C.) so that it can be readily combined with anti-microbial agents that are unstable at high temperature. Also, the polymer should not become brittle as the other components dissolve or leach out, so that the matrix does not break apart readily when handled.

Preferred polymers for the support resin include polystyrene, polyurethane, ethylene vinyl acetate, polyethylene, styrene/rubber, and ethylene/propylene. The more preferred support resin is an ethylene vinyl acetate polymer. Most preferably the ethylene vinyl acetate polymer includes between 5% and 50% vinyl acetate, and has a softening point of between 100° C. and 35° C., respectively.

A water-soluble substance, as used herein, is a substance that is sufficiently soluble in water that it will dissolve out of the matrix during contact with water to form channels in the matrix through which the anti-microbial agent will leach into the water. A further description of what constitutes a water-soluble substance is provided in the Other Embodiments section.

The preferred water-soluble substances are polymers. The preferred polymers are starches, polyvinyl alcohols, polyethylene oxides, hydroxyalkyl starches, hydroxyethyl and hydroxypropyl celluloses, and gelatins. The most preferred are polyethylene oxides, most preferably a Polyox having a molecular weight of between 100,000 and 5,000,000.

An anti-microbial agent is a substance that kills bacteria. The preferred anti-microbial agent for use in the matrix is chlorhexidine, most preferably the digluconate salt thereof; the hydrochloride and diacetate salts of chlorhexidine can also be used. Other anti-microbial agents that can be included in the matrix include tetracycline (and other antibiotics), and domiphen bromide.

Preferably, the matrix is a flat template having a thickness of up to 4 mm and is attached to the head of the body at the base of the bristles. The preferred templates have a surface area of at least 0.01 in$^2$, more preferably at least about 0.1 in$^2$. Most preferably, the template has the same surface area as the toothbrush head (minus the bristles). In this position the template is exposed to water when the brush is rinsed and to saliva when it is inserted into the mouth, and can supply the anti-microbial agent to the bristles for self-sterilization and to the mouth to kill bacteria. The matrix can also be attached to any other part of the brush (e.g., the back of the brush head or at the junction of the brush head and handle), provided that the part of the brush it is attached to is sufficiently close to the head end that it typically is inserted into the mouth during use.

In other preferred embodiments, the matrix includes two layers, joined together. By "two layers", it is meant that one section of the template has a different composition than a second section. The first outer layer includes a support resin or a water-soluble polymer, and an anti-microbial agent; the second inner layer includes the support resin. Significantly, the first layer can include a large quantity of anti-microbial agent because the layer includes less (or none) of the support resin, yet the layer is stable because the co-extruded second layer provides the necessary support. The second layer may also include, optionally, some water-soluble polymer and/or anti-microbial agent.

The invention features, in another aspect, an oral brush that includes a template including a water-soluble polymer and an anti-microbial agent.

The invention features, in another aspect, a matrix including ethylene vinyl acetate, polyethylene oxide, and an anti-microbial agent such as chlorhexidine. The matrix can be sized, shaped, and otherwise designed for short or long term placement at some point in the mouth. The matrix can also be designed as a template for inclusion on a toothbrush, or can be used to coat dental floss, or other dental instrument (s).

The matrices of the invention provide a controlled release of an anti-microbial agent into the mouth. When included on a toothbrush, the matrix repeatedly supplies controlled dosages of the agent to kill bacteria in the mouth and on the bristles of the brush. The matrices are easy to manufacture, and their composition, shape and thickness can be adjusted to provide the best properties for the intended use. For example, the amount and type of polyethylene oxide in the preferred embodiment can be modified so that the viscosity of the released polymer in solution is less than the viscosity of the saliva in the mouth.

Another aspect of the invention features a wear-indicator oral brush that includes a matrix containing a colorant (e.g., a dye) and a water-leachable substance that is released from the matrix when the oral brush is used to cause the matrix to change color after repeated (at least 5) typical uses. The preferred matrix is a template that includes two co-extruded or co-molded layers. The outer layer, which contacts water and saliva during brushing, preferably includes the water-leachable substance, which can be, for example, a water-soluble polymer like polyethylene oxide, or the colorant itself, or a combination of the two. The second, inner, layer preferably includes a support resin, and can also include a colorant (e.g. TiO$_2$) that provides the template with a different color, or shade of color, than the colorant included in the outer layer. The first layer preferably also includes a support resin, although less than the amount included in the second layer, and also can include an anti-microbial agent.

The oral brushes having a matrix including a colorant, i.e., pigment or dye, provide a means to monitor the degree of wear of the brush. Where the water-leachable substance includes the colorant, over time as the brush is used the colorant is released, causing the matrix to change color. In those embodiments in which the colorant is not water-leachable and thus is not released from the matrix, typically the portion of the template including a water-leachable substance dissolves away through repeated use of the brush to expose the section of the matrix that includes the colorant, providing an indication of wear. The amounts and types of colorant in the matrix can be adjusted so that the color of the matrix changes after the number of uses through which a typical brush should be used. When the colored matrix also includes an anti-microbial agent, the change of colorant can be designed to correspond with the depletion of the agent in the matrix.

Other features and advantages of the invention will be apparent from the description of the preferred embodiment thereof, and from the claims.

DESCRIPTION OF THE PREFERRED EMBODIMENT

Figure 1:
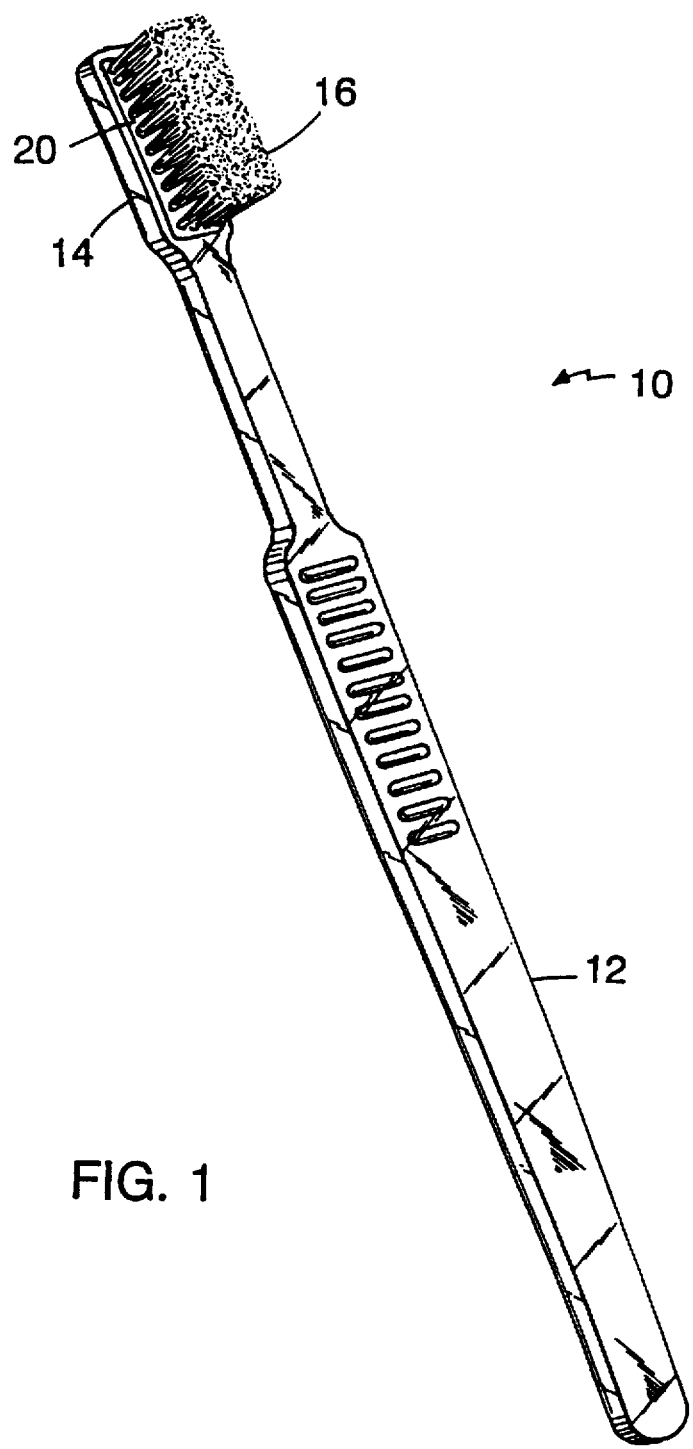

FIG. 1 is a perspective view of the preferred toothbrush.

FIGS. 2a–2e provide perspective views of some alternative two-layer templates. FIG. 2f is a cross-sectional view of the template of FIG. 2e, taken along line A—A. In these figures the holes through which the bristles would be inserted are not shown.

Referring to FIG. 1 a toothbrush 10 includes a plastic body having a handle 12 and a head 14 attached to a bristle portion 16. Also attached to the head at the base of the bristles is template 20, a sustained-release matrix.

The body of the toothbrush is formed by conventional methods well-known in the art. The handle is shaped to be grasped by a hand, but alternatively can be shaped to fit into an electric toothbrush. The configuration of the head can vary and may be oval, convex curved, flat trim, or serrated V, or any other desired configuration. The shape and size of handle 12 and head 14 can vary and the axes of the handle and head may be on the same or a different plane. The bristle portion is formed of tufts of individual filaments attached to the head in manners known to the art. Preferred filaments are those formed of polyamide and polyester. The filaments preferably have substantially uniform longitudinal lengths of between 0.3 and 6 cm, and substantially uniform cross-sectional dimensions between about 110 to about 350 microns.

There are three types of preferred templates.

1. Single-layer template including chlorhexidine

The single-layer template consists of a resin, ethylene vinyl acetate; a water-soluble polymer, Polyox; and an anti-microbial agent, chlorhexidine digluconate.

Ethylene vinyl acetate is the backbone of the matrix and has negligible solubility in water. It provides the matrix with its structural integrity when the other components of the matrix leach out during use. Ethylene vinyl acetate has low toxicity and grades are available that have low processing temperatures. Importantly, ethylene vinyl acetate maintains the integrity of the matrix without becoming stiff and brittle.

A sufficient amount, preferably greater than 50 percent by weight, of ethylene vinyl acetate should be included in the matrix so that when the other components leach out there is still enough resin present to maintain the structure of the matrix. Of course, not so much should be included that the matrix cannot be loaded with a sufficient amount of the water-soluble polymer and anti-microbial agent; preferably, the matrix should include less than 90 percent of the ethylene vinyl acetate by weight.

The ethylene vinyl acetate polymer used in the matrix preferably should contain between 5 percent and 50 percent by weight vinyl acetate. If the polymer includes too little vinyl acetate, the matrix may be too stiff and require higher processing temperatures. If the polymer includes too much vinyl acetate, the matrix may be rubber-like and too soft to process.

Polyox water-soluble resins are non-ionic ethylene oxide homopolymers that range in molecular weight from about 100,000 and 5,000,000. Polyox has a very low degree of toxicity, and grades are available that have a low processing temperature, and are completely water soluble in cold and warm water.

The preferred Polyox, available from DuPont, is WSR N-750, which has a molecular weight of 300,000. WSR N-750 has a water solubility that is sufficient to provide a controlled-release of the anti-microbial agent from the matrix at bactericidal levels, but the solubility in the matrix is low enough that it dissolves out slowly, over a period of many uses.

The matrix preferably contains between 5 percent and 40 percent Polyox WSR N-750 by weight. If too much Polyox is included, the anti-microbial agent may leach out too quickly, and the structural integrity of the matrix once most of the Polyox has leached out may be adversely affected. If too little Polyox is included, too low a quantity of the anti-microbial agent may be released from the matrix during use.

The preferred anti-microbial agent is chlorhexidine digluconate, which is well-known for its gingivitis-prevention properties. The amount of chlorhexidine included in the matrix depends on the level of the desired dosage and amount of Polyox; preferably, the matrix includes between 1 percent and 30 percent of chlorhexidine digluconate by weight. If too high a level of chlorhexidine is included, the matrix may become brittle. Of course, a sufficient amount of the agent should be included so that enough is released during use to be effective.

The template should be formed to fit to the shape of the head at the base of the bristles, and should be as thick as possible to allow for many uses before all of the anti-microbial agent is leached out. Preferably, the template is at least 0.5 mm thick to ensure adequate mechanical strength, and can be up to at least 4 mm thick.

In use, the toothbrush is rinsed with water, toothpaste applied, and then the head of the brush is inserted into the mouth to brush the teeth with the bristles. Upon contact with water some of the anti-microbial agent diffuses out of the matrix, onto and down the bristles, and eventually into the saliva of the mouth, killing bacteria on contact. As the Polyox slowly dissolves with repeated uses of the brush, water is allowed to penetrate into the matrix, making more of the anti-microbial agent accessible by diffusion from the matrix core. Eventually, all of the Polyox and agent have left the matrix, and the toothbrush is discarded.

The matrix is designed to incorporate the desired criteria of release rate, dosage, and effective template lifetime by adjusting the thickness of the template included on the brush, the quantity of anti-microbial agent contained in the matrix, and the quantity of Polyox, or other water-soluble polymer, included in the matrix. The higher the desired dosage, the greater the quantity of water-soluble polymer and agent included in the matrix. Also, to increase the released dosage, a more water-soluble form of Polyox can be employed. The lifetime of a given matrix can be increased by increasing the thickness of the template.

Examples of preferred matrices were made by the following procedure.

Materials a. Chlorhexidine digluconate

A 20 percent solution of chlorhexidine digluconate, available from Pliva Pharmaceutical, Chemical, Food, and Cosmetic Industry of Zagreb, Yugoslavia, or ICI, was freeze-dried as follows:

1. Measure 500 ml of chlorhexidine digluconate in a graduated cylinder and transfer it to a 1 liter flask.
2. Adjust volume to 1 liter with double distilled filtered water and mix together.
3. Transfer 300 ml. portions of mixture to glass evaporating dishes (8 inch diameter).
4. Place all evaporating dishes in the freeze-drying apparatus until all water is removed.
5. Transfer the chlorhexidine freeze-dried powder to a 1 liter glass bottle and cap.
6. Store the bottle in a refrigerator or a dark room at approximately 4° C.

b. Ethylene Vinyl Acetate

The most preferred ethylene vinyl acetate is sold by DuPont under the tradename ELVAX 360, and has a vinyl acetate content of 25 percent by weight; a tensile strength of 18.0 Mpa at 23° C. (ASTM D638); an elongation of 800 percent at 23° C. (ASTM D638); a softening temperature of 53° C. (ASTM D1525); and a flexural modulus of 26 Mpa at 23° C. (ASTM D790). ELVAX 360 contains 500 ppm BHT as an anti-oxidant.

In order to mix with chlorhexidine and Polyox powders, ELVAX 360 pellets are ground into powders with particle sizes of less than 250 microns with a Glen Mill Granulator (Model #CS 150/100-2) installed with a screen plate having 1 mm screen holes. A suction system is added to the grinding chamber to facilitate the removal of powders from the chamber to a container. During grinding, the material is recycled through the grinder as many times as necessary (usually two or three passes) to meet the size requirement. A sieve shaker manufactured by the W. S. Tyler Co. is used to control the sizes as needed.

c. Polyox

Polyox WSR N-750 is available from Union Carbide, and has a melting point of 62°–67° C. and a molecular weight of 300,000. The Polyox is used as received and mixed with other components to form the template.

d. Blending of Materials

The ELVAX 360, Polyox, and chlorhexidine digluconate are mixed in a blender. Each component is first weighed and then poured into a glass jar with a capacity of 0.5 kilograms. The jar is then placed on a ball-mill rotator and mixed for approximately ½ hour. For a quantity greater than 0.5 kilograms, a V-blender manufactured by Patterson-Kelly Co. Inc. is used. The blended material should be stored in a dry, cool room.

e. Processing

The conventional equipment used to produce the matrix includes an extruder, a cooling plate, and a puller. An extrusion die with an opening of 2" wide is used. To control the thickness of the template, the die utilizes a flexible lip design which enables the die lip to be adjusted anywhere from 0.15" to 0.45". Each die is supplied with a sensor for the recording of melt pressure and temperature. Pulling speed are adjusted to produce a 1" wide strip with a thickness of 0.020" or 0.040". The strip can then be fabricated into templates.

Samples were made with both a twin-screw and single-screw extruder. The Werner & Pfleiderer 30 mm twin-screw extruder is based on a corotating and intermeshing twin-screw system. To minimize Polyox and chlorhexidine degradation during processing, the twin screws consists of only two high-shear kneading elements and the rest being low-shear conveying screw elements; the screw speed and processing temperatures are reduced to a minimum. The mixture is fed using a K-Tron twin-screw feeder (Model T-20).

Alternatively, a Haake ¾ inches single-screw extruder equipped with a 5 HP drive motor is employed. When making the most preferred matrix, the extruder was operated with a screw speed of 35 rpm, a barrel pressure of 70 psi, a die pressure of 80 psi, barrel temperature of 113° C., and a die temperature of 113° C.

The blend of materials is fed to either extruder and the strip produced is pulled onto a plate by a Ferris puller at a speed of between three or four feet per minute with minimum tension on the strip. The strip is cooled on a plate placed inside a PVC tube by blowing dry compressed air into the tube at approximately 10 CFM. The finished product should be kept in a cool, dry room.

The matrices can also be made by other conventional processes, such as by injection molding, casting foam dispensing machines, and reaction injection molding. In addition, two color injection molding can be used to make the toothbrush/matrix combination.

Toothbrush Preparation

Toothbrushes including the sustained-release matrix were prepared according to the following procedure:

1. Toothbrush handles with undercuts on the toothbrush head for placing templates were molded.

2. The strips prepared above were cut into two strips having maximum width of 39/64". Tape was used to hold the material to prevent stretching.

3. Sets of holes corresponding to the desired bristle pattern to be used with the brush were punched with a Dake arbor press.

4. Templates of the desired size were cut from the strips, and glued to the head of the toothbrush body.

5. The bristles were attached to the head by standard procedures.

Testing for Sustained-Release Properties

The sustained-release matrices of the invention can be tested for their long-term release profiles according to the following procedure.

First, a calibration plot of chlorhexidine digluconate in distilled water was prepared over concentration range of 2 to 40 mcg/ml. Release studies were performed in triplicate; the procedure is summarized below:

1. Samples (½"×1") were cut from the strip by random sampling.

2. The samples were placed in 250 ml beakers, which were then set into a shaking water bath (37° C., 80 rpm).

3. 5 ml of distilled water were pipetted to each beaker.

4. After 5 minutes, the samples were removed from beakers and assayed for chlorhexidine content in release solution by uv-spectrophotometric analysis.

5. This procedure was repeated for 100 release periods.

The preferred strips showed excellent chlorhexidine release characteristics over extended periods of use. The composition of the preferred strips, and their release properties after 100 uses, are summarized in the Table below. In the Table, EVA is the preferred ethylene vinyl acetate discussed above; the Polyox is either the more preferred WSR N-750, or a 60:40 blend (60% Polyox coagulant grade, 40% WSR N-750 from Union Carbide); CHG is chlorhexidine digluconate; "S" means the template was prepared by single-screw extrusion, "T" by twin-screw extrusion; [CHG] (ppm) is the concentration of CHG in ppm in the release solution at 100 releases and 60 m (60 mesh) or 18 m (18 mesh) is the particle size of chlorhexidine digluconate employed (no particle size listing indicates that the chlorhexidine was not sieved following freeze-drying). All of the templates were still releasing over 1 ppm chlorhexidine after 100 uses. The most preferred matrix is 2 mm thick and includes 60% EVA, 15% Polyox WSR N-750, and 25% chlorhexidine digluconate.

| Thickness (mm) | Composition (%) | | | | | [CHG] (ppm) |
|---|---|---|---|---|---|---|
| | EVA | Polyox | | CHG | | |
| 1.0 | 70 | 15 | (60:40) | 15 | ICI      S | 5.51 |
| 1.0 | 65 | 15 | (60:40) | 20 | ICI      S | 6.49 |
| 1.0 | 70 | 15 | (N-750) | 15 | ICI      S | 20.98 |
| 0.5 | 70 | 15 | (60:40) | 15 | ICI      S | 1.32 |
| 0.5 | 70 | 15 | (N-750) | 15 | ICI      S | 1.57 |
| 0.5 | 70 | 15 | (N-750) | 15 | ICI      S | 2.19 |
| 0.5 | 70 | 15 | (N-750) | 15 | ICI      S | 2.53 |
| 1.0 | 65 | 20 | (N-750) | 15 | ICI      S | 8.63 |
| 1.0 | 60 | 25 | (N-750) | 15 | ICI      S | 12.41 |
| 1.0 | 50 | 35 | (N-750) | 15 | ICI      S | 7.04 |
| 1.0 | 70 | 15 | (N-750) | 15 | ICI      T | 7.84 |
| 1.0 | 70 | 15 | (N-750) | 15 | ICI      T | 23.15 |
| 1.0 | 70 | 15 | (N-750) | 15 | ICI      T | 2.73 |
| 1.0 | 70 | 10 | (N-750) | 20 | ICI      T | 21.38 |
| 2.0 | 65 | 15 | (N-750) | 20 | (60m ICI)    S | 17.59 |
| 2.0 | 70 | 15 | (N-750) | 15 | (Pliva)      S | 12.43 |
| 2.0 | 65 | 20 | (N-750) | 15 | (60m ICI)    S | 7.62 |
| 2.0 | 70 | 15 | (N-750) | 15 | (60m ICI)    S | 11.20 |
| 2.0 | 70 | 15 | (N-750) | 15 | (18m ICI)    S | 6.78 |
| 2.0 | 70 | 15 | (N-750) | 15 | (60m ICI)    T | 9.10 |
| 2.0 | 65 | 20 | (N-750) | 15 | (60m ICI)    T | 9.08 |
| 2.0 | 70 | 15 | (N-750) | 15 | (Pliva)      T | 1.53 |
| 2.0 | 60 | 15 | (N-750) | 25 | (60m ICI)    T | 50.76 |
| 2.0 | 65 | 15 | (N-750) | 20 | (60m ICI)    T | 7.67 |
| 2.0 | 60 | 15 | (N-750) | 25 | (60m Pliva)  T | 9.83 |
| 2.0 | 55 | 15 | (N-750) | 30 | (60m Pliva)  T | 7.10 |
| 2.0 | 60 | 15 | (N-750) | 25 | (60m ICI)    S | 63.00 |
| 2.0 | 55 | 10 | (N-750) | 35 | (60m Pliva)  T | 15.78 |
| 2.0 | 60 | 15 | (N-750) | 25 | (18m ICI)    S | 62.34 |
| 2.0 | 60 | 15 | (N-750) | 25 | (60m Pliva)  | 47.22 |
| 2.0 | 60 | 15 | (N-750) | 25 | (Pliva)      S | 72.63 |
| 2.0 | 60 | 15 | (N-750) | 25 | (Pliva)      T | 29.72 |
| 2.0 | 60 | 15 | (N-750) | 25 | (ICI)        S | 54.56 |
| 2.0 | 60 | 15 | (N-750) | 25 | (ICI)        T | 31.37 |
| 2.0 | 60 | 15 | (N-750) | 25 | (60m Pliva)  S | 61.24 |
| 2.0 | 60 | 15 | (N-750) | 25 | (60m Pliva)  S | 60.03 |
| 2.0 | 60 | 15 | (N-750) | 25 | (60m Pliva)  S | 60.43 |

2. Two-layer template including chlorhexidine

The preferred single-layer template generally includes over 50% support resin (EVA) by weight to achieve good mechanical properties and processibility. This, to some extent, limits the quantity of chlorhexidine that can be included in the matrix. An alternative two-layer template provides a higher quantity of chlorhexidine in the portion of the template that primarily contacts water and saliva. The first, outer layer contains less ethylene vinyl acetate and more polyethylene oxide and chlorhexidine. The second, inner layer has the composition of the preferred single-layer embodiment, although the second layer could consist entirely of ethylene vinyl acetate. A preferred two-layer matrix includes 65% ethylene vinyl acetate, 15% Polyox, and 20% chlorhexidine digluconate in the inner layer, and 30% ethylene vinyl acetate, 25% Polyox, and 45% chlorhexidine digluconate in the outer layer. The inner layer should include at least 60% of the support resin; the outer layer can include upwards of 50% chlorhexidine.

The outer layer releases a higher dosage of chlorhexidine when contacted with water, yet has good strength and processibility because the second layer provides the necessary support. As the outer layer wears away, the antimicrobial agent in the inner layer also is released. The outer layer preferably is 0.25 to 3 mm thick, while the inner layer preferably is 0.1 to 0.5 mm thick.

The two-layer templates can be produced either by conventional co-extrusion or co-injection molding techniques, from two different mixtures. Alternatively one layer can be extruded and then the other layer can be thermoformed/compression molded or laminated onto the extruded layer.

An alternative two-layer embodiment has an outer layer consisting only of the support resin and the anti-microbial agent. The preferred anti-microbial agent, chlorhexidene digluconate, is water-soluble, although not to the same degree as the water-soluble polyethylene oxide. Because the outer layer includes a high quantity of the anti-microbial agent, enough of the agent can dissolve out of the matrix to provide a sufficient dosage of the agent without the assistance of a water-soluble polymer.

3. Template including a colorant

The wear-indicator template preferably includes two layers, each with a different colorant. The outer layer includes a water-soluble polymer (preferably polyethylene oxide, polyethylene glycol, or polyvinyl alcohol) and a colorant, preferably a water-leachable colorant; a support resin is optional. The inner layer includes a support resin and a second colorant, like titanium dioxide, which provides a solid white appearance. The different colorants should be selected to provide a clear contrast so that a user can plainly discern the color change as the colorant in the outer layer leaches out over time.

The two-layer templates including a colorant can be produced by the same techniques used to produce the two-layer templates including an anti-microbial agent discussed above.

Figure 2A:
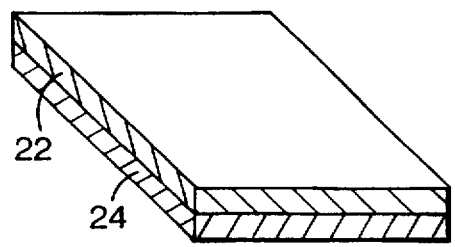

The preferred wear-indicating template is illustrated in FIG. 2a and consists of an outer layer 22, which includes the colorant that is released during use, and an inner layer 24, which is adjacent the toothbrush during use. Inner layer 24 includes titanium dioxide.

Alternative two-layer template embodiments are illustrated in FIGS. 2b–2f. In these embodiments, no colorant is included in the outer layer 26 and a non-white colorant is included in the inner layer 28. The outer layer in these embodiments preferably consists only of water-soluble polymer; as the outer layer dissolves away during use the colorant in the second layer becomes visible, or more visible, providing an indication of the degree of wear of the brush.

Figure 2B:
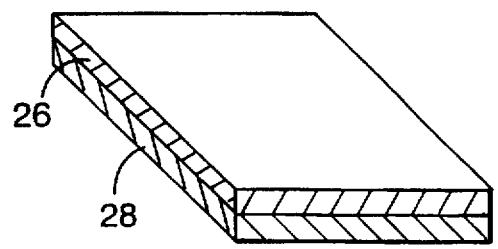

Referring to FIG. 2b, a template has a flat outer layer 26 and a flat inner layer 28 that are approximately the same size. As outer layer 26 dissolves away with repeated use, a colorant in inner layer 28 becomes visible to a user looking straight down at the surface of the bristles that contact the teeth.

Figure 2C:
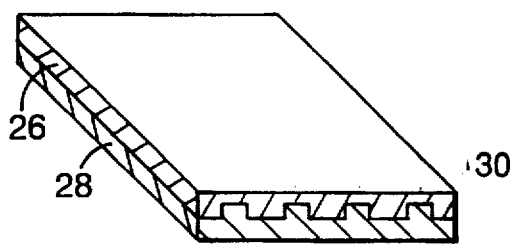
Figure 2D:
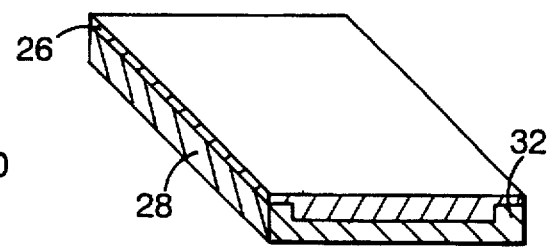

Referring to FIG. 2c, inner layer 28 of a template has elements 30 that extend into grooves in outer layer 26. As outer layer 26 dissolves away, elements 30, which include colorant, become visible to the user as stripes at the base of the bristles. A similar embodiment is illustrated in FIG. 2d, except that elements 32 extend along the exterior of outer layer 26. In this embodiment, as outer layer 26 dissolves away a colored strip along the edge of the template becomes visible to a user looking straight down at the surface of the bristles that contact the teeth.

Figure 2E:
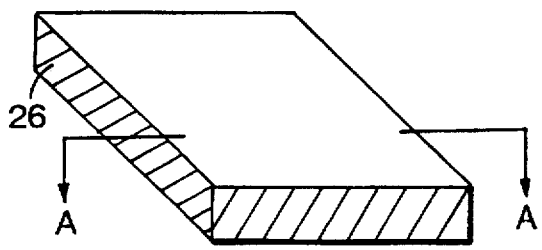
Figure 2F:
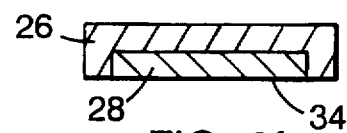

Referring to FIGS. 2e and 2f, an alternative template includes an inner layer 28 that is fully surrounded by the outer layer 26 except at surface 34, where the template is attached to the head of the brush. As outer layer 26 dissolves, inner layer 28 becomes visible from the sides and from the top.

Although not illustrated, other alternative matrices include those in which the inner layer(s) is simply two narrow strips, like elements 30; and those in which the inner layer includes cyclindrical elements that extend upwards from the inner layer into the outer layer. In the latter embodiment, as the outer layer dissolves away the inner layer becomes visible as colored dots.

The following examples were made from two ¾ inch extruders with a co-extrusion die to produce two-layer templates having the design shown in FIG. 2a and having a thickness of about 10 mm.

EXAMPLE A

The first layer of the template consisted of 44.6% ethylene vinyl acetate (Elvax 360), 44.5% Polyox N-750, 10% polyethylene glycol (Dow-E4500), and 0.9% of a dark blue pigment (FD&C Blue No. 2, Aluminum Lube 35–42%, available from Warner Jenkinson of St. Louis, Mo.). The second layer consisted of 99.5% Elvax 360 and 0.5% titanium dioxide. When the template was submerged in water for 24-hours, the initial dark blue color changed to a light blue.

EXAMPLE B

The first layer of the template includes 49.5% Elvax 360, 49.5% Polyox N-750, and 1% dark blue pigment. The second layer was the same as in Example A. The results of a 24-hour water-submerge test also were the same.

EXAMPLE C

The first layer of the template consists of 99% polyvinyl alcohol and 1% of the dark blue pigment, and no support resin. The second layer was the same as for the other two examples. When this template was subjected to a 24-hour water-submerge test, the initial dark blue color of the template turned to white.

OTHER EMBODIMENTS

Other embodiments are within the claims. For example, other water-insoluble polymers can be used as the support resin. To determine whether a polymer can be used as a support resin within the meaning of this application, a template should be prepared containing 60% of the polymer, 15% Polyox WSR N-750, and 25% chlorhexidine digluconate. Matrix samples (½"×1") having a thickness of 2 mm are placed in 250 ml beakers which are then set into a shaking water bath (37° C., 80 rpm) for 8 hours. If the matrix has maintained its structural integrity in the bath and does not fall apart, the polymer is a support resin. Examples of the specific polymers that can be used in place of EVA as the support resins include Hytrel G-4074 (a polyester available from DuPont); Hytrel 4056 (a polyester elastomer also available from DuPont); Vestenamer 8012 (TPE, available from Huls America); Rimplast PSW 2159 (a silicone, available from Petrarch Systems); Prolytropes (an ethylene/propylene alloy available from A. Schulman, inc.); Millathanes (a polyester urethane available from Millathane); Kraton G-7680 (a styrene/rubber available from Shell Chemical); and Santoprene 101-55 (a polyolefin alloy available from Monsanto Chemical). Prolytropes and Kraton G-7680 are more preferred because of their relatively low processing temperatures, 29° C. and 57° C., respectively. Examples of other general classes of polymers that can be used as support resins include polyurethanes, polycarbonates, polyesters, polyethylenes, polypropylenes, polystyrenes, and polyvinyl chloride; polyurethanes, polyethylenes, and polystyrenes are more preferred because forms of these polymers with relatively low processing temperatures are available.

Additionally, other water-soluble substances can be used in place of Polyox in the matrix. To determine whether something is a water-soluble substance within the meaning of this application, a template should be prepared containing 80% EVA and 20% of the substance. Matrix samples (½"× 1") having a thickness of 2 mm are placed in 250 ml beakers which are then set into a shaking water bath (37° C., 80 rpm) for 8 hours. After that time, the matrix is removed, and photomicrographs (magnification of 350×) of the matrix after the procedure are compared to photomicrographs (350×) of the matrix prior to the procedure. If after the procedure channels and pores have formed into the matrix, the substance is a water-soluble substance. Other water-soluble natural polymers than can be used include agar; carrageenan; corn starch; guar gum; gum arabic; gum karaya; gum tragacanth; locust bean gum; potato, wheat and rice starches; tapioca; casein; pectin; and sodium alginate. Modified natural polymers then can be used include cationic starch; dextran; hydroxyalkyl starches; hydroxyethyl and hydroxypropyl cellulose; methyl cellulose; sodium carboxymethyl cellulose; xanthan gum; gelatin; and sodium carboxymethyl starch. Synthetic polymers suitable for use include polyvinyl alcohol; cationic resins and quaternary ammonium compounds; poly (N-vinyl-2-pyrrolidinone); vinyl ether polymers; styrene-maleic anhydride copolymers; ethylene-maleic anhydride copolymer; hydrophilic gels; and polymeric surface-active agents. Inorganic salts, (e.g., EDTA, NaCl, $Na_2CO_3$, and KCl) and fillers may also be used.

Anti-microbial agents that can be used in place of chlorhexidine digluconate include antibiotics such as actinobolin, chlortetracycline, tetracycline, streptomycin, kanamycin, neomycin, niddamycin, bacitracin, erythromycin, penicillin, rancemycin, gramicidin, saramycin, and polymyxin B; as well as antiplaque enzymes such as mucinases, pancreatin, fungal enzymes, protease-amylase, dextranase, moimnase, zendium, amyloglucosidase, and glucose oxidase. Other conventional antimicrobials that can be used include phenolic compounds (e.g., phenol, thymol, 2-phenylphenol, hexylresorcinol), and listerine (thymol, eucalyptol, menthol, methylsalicylate); bi-pyridines (e.g., octenidene); pyrimidines (e.g., hexetidine); halogens (e.g., iodine, iodophores, fluorides); quaternary ammonium salts (e.g., cetylpyridinium chloride, benzethonium chloride, domiphen bromide); oxygenating agents (e.g., peroxides; perborate); herbal extracts (e.g., sangnimarine); heavy metal salts (e.g., silver, mercury, zinc, copper, tin); and other bis-biguanidines besides chlorhexidine (e.g., alexidine). Of course, other chlorhexidine salts like the diacetate and dihydrochloride can be used in place of chlorhexidine digluconate.

Moreover, the matrices can be used in other ways, for example by impregnating the bristles of a toothbrush with small matrix particles, by inserting the matrices into the holes the toothbrush head into which bristles are then inserted, or by coating the matrix on dental floss. The matrix also can be attached to the side of the head of the toothbrush opposite the side to which the bristles are attached. Alternatively, a matrix can be designed to be inserted and left in the mouth for an extended period of time, for example as a small ring that fits around a tooth.

Templates can be designed that are sustained-release but that do not release over 1 ppm chlorhexidine after 100 uses by the test previously designed. For example, a disposable toothbrush, which would be discarded after only a few uses, does not require such extended release lifetime. For the purposes of this invention, sustained-release means that the matrix still releases at least 1 ppm of the anti-microbial agent after 10 uses (more preferably after 50 uses) when tested according to the procedure described in the Preferred Embodiment section.

Any of the two-layer templates shown in FIG. 2 can be used to provide the sustained-release of an anti-microbial agent.

Further, other well-known, conventional additives such as fillers, binders, lubricants, and channeling agents can be included in the matrix, although care should be taken that these additives do not adversely affect the agent release rate.

We claim:

1. A method of providing an indication of wear in an oral brush, comprising brushing teeth with an oral brush comprising a body including a handle and head, a brush portion connected to said head, and a wear-indicator composite, attached to said body, comprising a water-insoluble support resin, a water-soluble polymer, and a colorant, wherein during said brushing the wear-indicator composite contacts water, said water-soluble polymer dissolving in said water resulting in the release of said colorant from said composite.

2. The method of claim 1 wherein said water-soluble polymer comprises polyethylene oxide.

3. The method of claim 1 wherein said composite further comprises an anti-microbial agent.

4. A method of providing an indication of wear in an oral brush, comprising brushing teeth with an oral brush comprising a handle and head, a brush portion connected to said head, and a wear-indicator composite, separate from said brush portion, attached to said body, comprising a blend of a water-insoluble resin and a colorant, wherein during said brushing the wear-indicator composite contacts water, resulting in the release of said colorant from said composite.

5. The method of claim 4 wherein said wear-indicator composite comprises a template between 0.5 mm and 4 mm thick and said template is inserted into said mouth wherein said oral brush is inserted into said mouth during brushing.

6. The method of claim 5 wherein said template further comprises a water-soluble substance.

7. The method of claim 4 wherein said water-insoluble resin comprises ethylene vinyl acetate.

8. The method of claim 1, wherein said water-soluble polymer is selected from the group consisting of polyethylene glycol and polyvinyl alcohol.

9. The method of claim 1 or 2, wherein said support resin comprises ethylene vinyl acetate.

10. The method of claim 3, wherein said anti-microbial agent comprises chlorihexidene.

11. The method of claim 1, wherein said brush portion comprises tufts of bristles.

12. The method of claim 6, wherein said water-soluble substance comprises polyethylene oxide.

13. The method of claim 12, wherein said water-insoluble resin comprises ethylene vinyl acetate.

* * * * *